US00PP21792P3

(12) United States Plant Patent
Pinochet

(10) Patent No.: US PP21,792 P3
(45) Date of Patent: Mar. 22, 2011

(54) **VARIETY OF *PRUNUS* ROOTSTOCK NAMED 'GREENPAC'**

(50) Latin Name: *(Prunus dulcis×P. persica)×(P. persica×P. davidiana)*
Varietal Denomination: Greenpac

(75) Inventor: Jorge Pinochet, Barcelona (ES)

(73) Assignee: Agromillora Iberia, S.L., Barcelona (ES)

( * ) Notice: Subject to any disclaimer, the term of this patent is extended or adjusted under 35 U.S.C. 154(b) by 0 days.

(21) Appl. No.: 12/456,559

(22) Filed: Jun. 18, 2009

(65) Prior Publication Data

US 2010/0325762 P1 Dec. 23, 2010

(51) Int. Cl.
*A01H 5/00* (2006.01)

(52) U.S. Cl. ..... Plt./180
(58) Field of Classification Search ..... Plt./180
See application file for complete search history.

(56) References Cited

PUBLICATIONS

Upov Plant Variety Database 2010/02 p. 1. Country/ Authority: QZ.*
Upov Plant Variety Database 2010/02 p. 1. Country/ Authority: CL.*

* cited by examiner

*Primary Examiner*—Annette H Para
(74) *Attorney, Agent, or Firm*—The Webb Law Firm

(57) ABSTRACT

A new and distinct hybrid peach-almond plant used as a rootstock that exhibits moderate root-knot nematode resistance, high productivity, and compatibility with peach, nectarine, almond, and plum varieties.

6 Drawing Sheets

Botanical classification: [(*Prunus dulcis×P. persica*)×(*P. persica×P. davidiana*)].

Varietal denomination: 'Greenpac'.

BACKGROUND OF THE INVENTION

The present invention comprises a new and distinct cultivar of peach-almond hybrid [(*Prunus dulcis×P. persica*)×(*P. persica×P. davidiana*)] used as a rootstock known by the varietal name 'Greenpac'. The new variety was discovered in Barcelona, Spain in 1999 as a result of a planned breeding program. The new variety is the result of a cross between 'Felinem' (*Prunus dulcis×P. persica*) (female parent, unpatented) and 'Cadaman' (*Prunus persica×P. davidiana*)(male parent, unpatented). The purpose of the breeding program was to develop rootstocks that are adaptive to Mediterranean conditions, with high vigor, low chilling requirements, a tolerance to calcareous soils, and good productivity. The new variety exhibits similar good tolerance to calcareous soils, moderate root-knot nematode resistance, and high vigor to both parents, but differs from both parents in its high productivity with peach and nectarine varieties and its smaller-sized leaves. Further, the new variety has similar peach-like leaves, productivity and root-knot nematode resistance similar to 'Nemaguard' (*Prunus persica×P. davidiana*) (unpatented), but differs from 'Nemaguard' in smaller-sized leaves, tolerance to iron chlorosis, and the fact that it does not propagate by seed. The new variety has been trial and field tested and has been found to retain its distinctive characteristics and remain true to type through successive propagations. The following characteristics distinguish 'Greenpac' from other varieties known to the breeder:

1. Small leaves;
2. Peach-like leaves;
3. No suckering;
4. Better tolerance to alkaline soils than most peach rootstocks;

5. Moderate resistance to root-knot nematodes (*Meloidogyne* spp.);
6. High productivity;
7. High in vitro propagation efficiency;
8. Excellent rate of bud take; and
9. Better drought tolerance than most peach varieties.

The following Tables provide additional differences between 'Greenpac' and its parental varieties:

TABLE 1

| 'Greenpac' | 'Felinem' (female parent) |
|---|---|
| Green leaves | Red leaves |
| Smaller sized leaves | Bigger sized leaves |
| No fructification | Generates fruit |
| Moderated resistance to root-knot nematodes | Low resistance to slight susceptibility to root-knot nematodes |

TABLE 2

| 'Greenpac' | 'Cadaman' (mate parent) |
|---|---|
| Smaller leaves; lanceolated elliptic shape | Bigger leaves; lanceolated elongated shape |
| Leaves curve backwards | Leaves straight |
| Leaf border is crenate | Leaf border is serrate |
| In vitro propagation easy | In vitro propagation difficult |
| Tolerant to iron chlorosis | Sensitive to iron chlorosis |
| No fructification | Generates fruit |
| Early blooming habit | Blooms 10 to 15 days later than 'Greenpac' |

DESCRIPTION OF THE DRAWINGS

The accompanying photographic drawings illustrate the new variety with the color being as nearly true as is possible with color illustrations of this type.

DESCRIPTION OF THE PLANT

Figure 1:
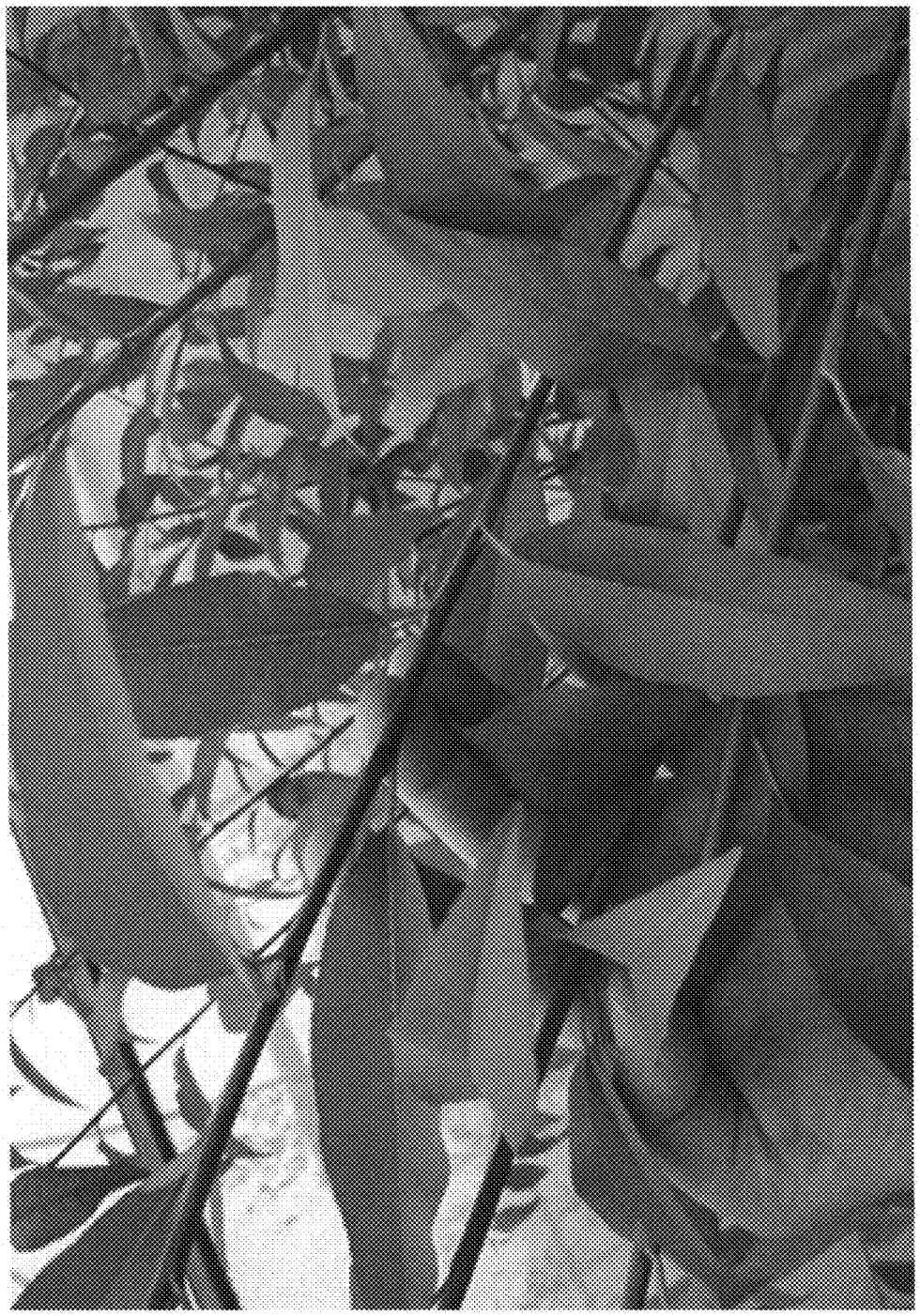
FIG. 1 shows the leaves of the new variety.
Figure 2:
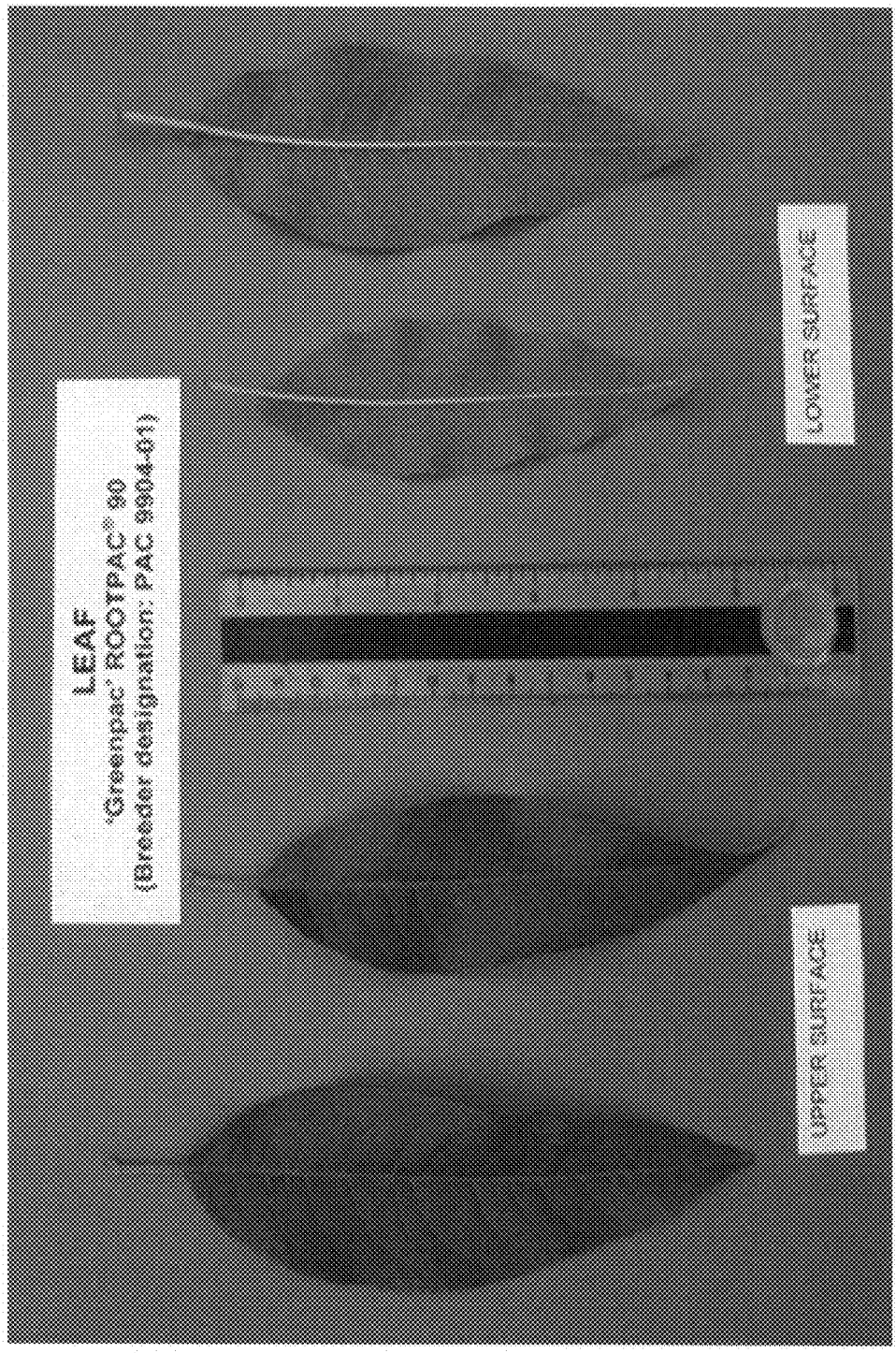
FIG. 2 shows the upper surface and the lower surface of the leaves of the new variety.
Figure 3:
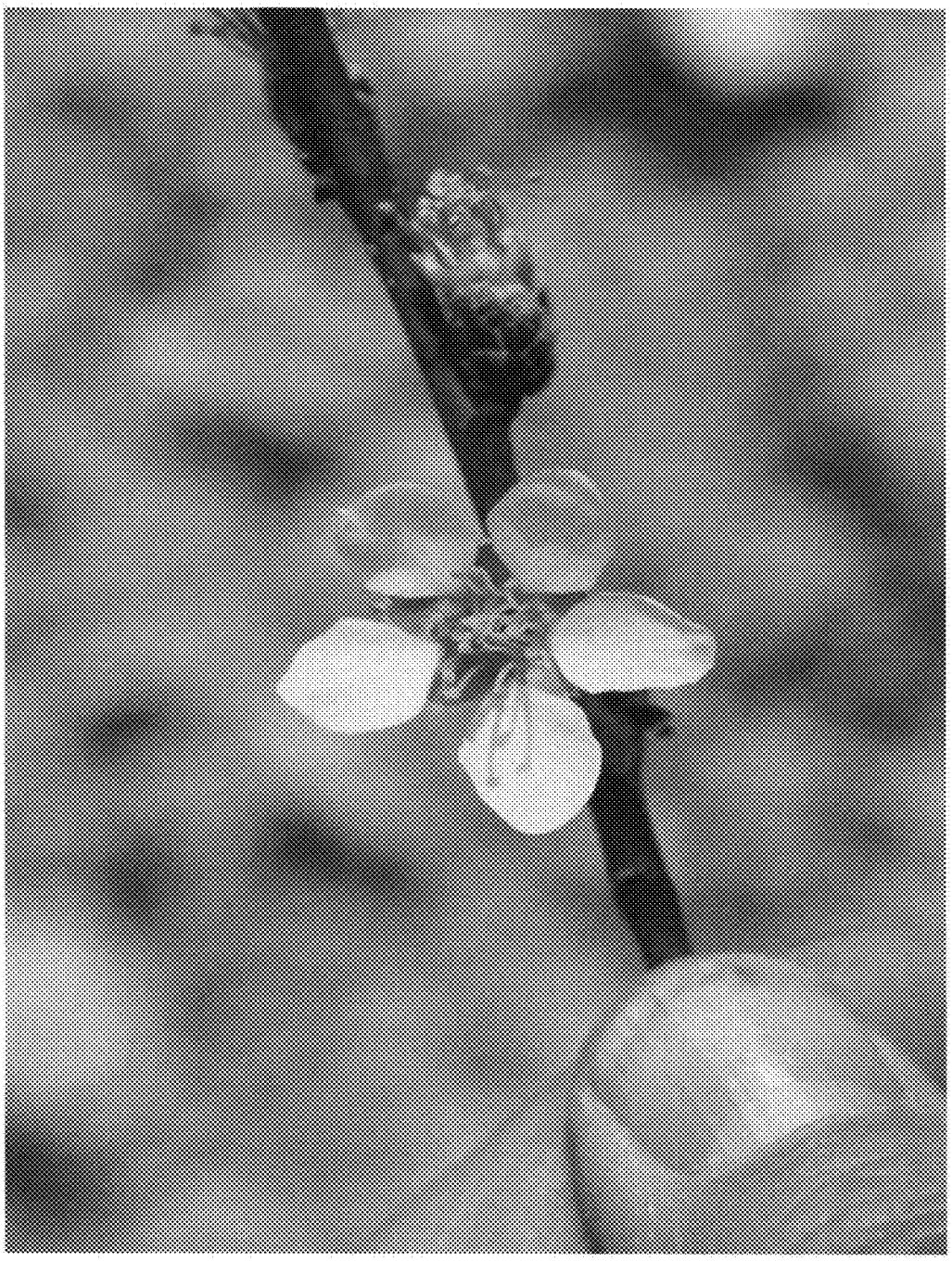
FIG. 3 shows the flowers of the new variety.
Figure 4:
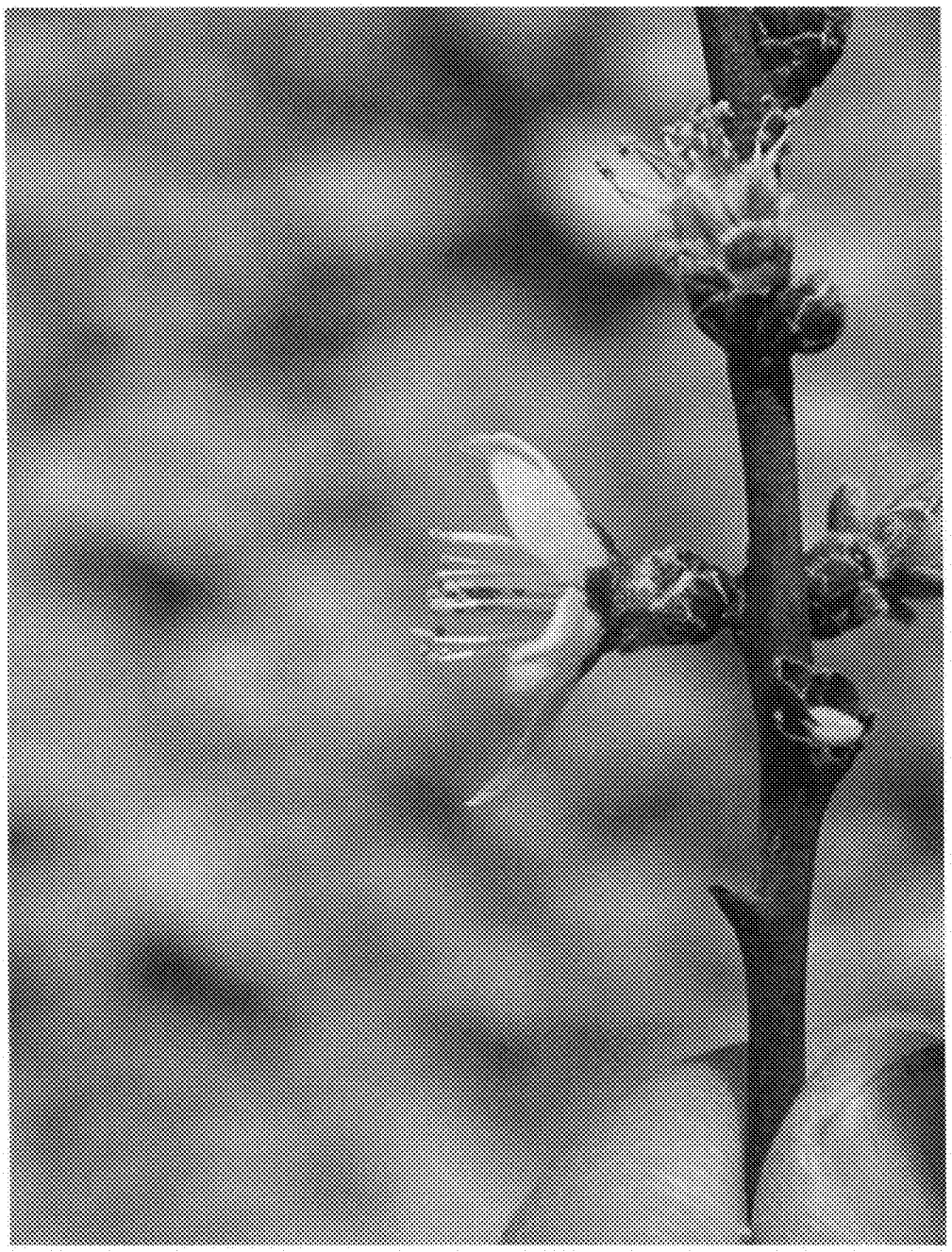
FIG. 4 is another photograph of the flowers of the new variety.
Figure 5:
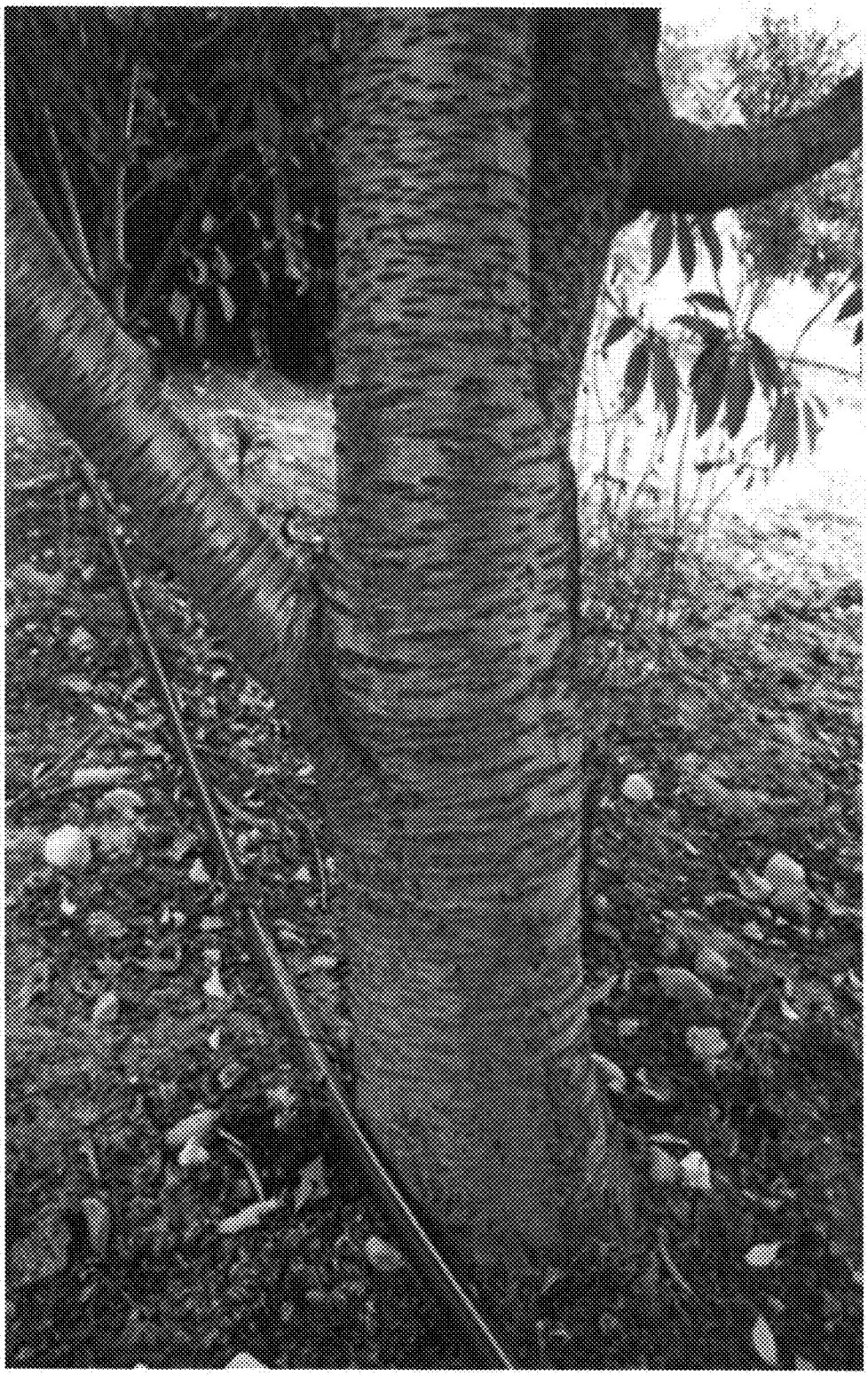
FIG. 5 shows the trunk of the new variety.
Figure 6:
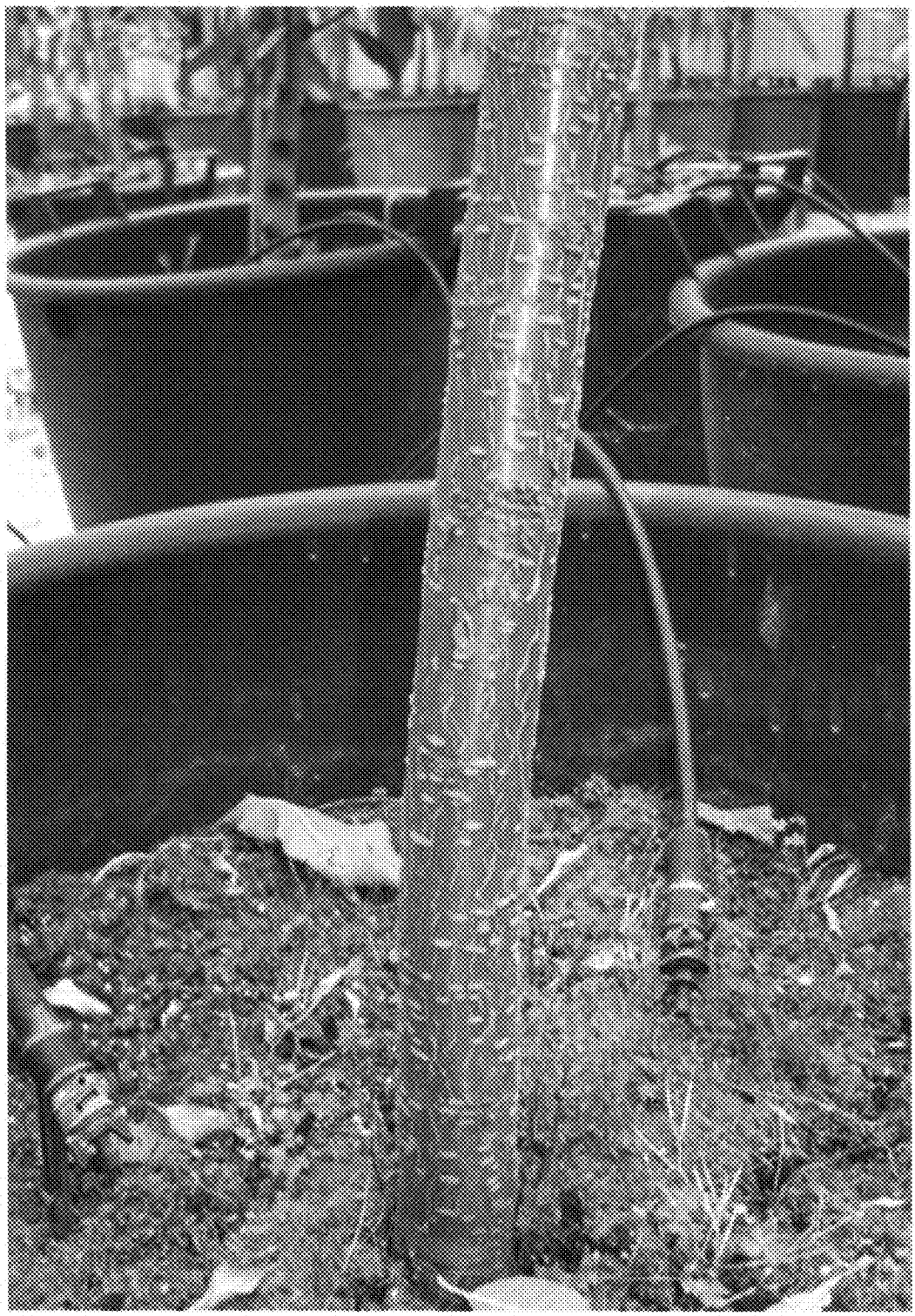
FIG. 6 is a photograph of a trunk of a 2 year old plant of the new variety.

The following detailed description sets forth the characteristics of the new cultivar. The data which defines these characteristics was collected under natural daylight on plants produced by asexual reproductions via in vitro propagation carried out in Barcelona, Spain. The plants were grown under normal field conditions with drip irrigation, as well as in 5 and 40 liter containers. Color designations are presented with reference to the "Dictionary of Color" by A. Maerz and M. Rea Paul, Second Edition (1950).

TREE

Age: 6 years.
Size: 3.8 meters tall.
Vigor: High.
Density: Medium.
Form: Compact.
Production: Abundant.
Growth type: Upright.
Bearing: Non-fruit bearing.
Pathogen resistance:
- *Fungal disease.*—Unknown.
- *Insects.*—Unknown.
- *Mites.*—Unknown.
- *Viruses.*—Plum pox virus (PPV/Sharka).
- *Other diseases.*—Root-knot nematodes (*Meloidogyne* spp.).

Rootstock performance:
- *Root sprouts* (*suckering*).—Not present.
- *Anchorage.*—Good with a big root system.
- *Compatibility.*—Compatible with peach, nectarine, almond, and plum varieties.
- *Vigor.*—High (similar to 'Nemaguard').

Trunk:
- *Size.*—Large; cylindrical and from 17 to 18 cm. in diameter.
- *Surface texture.*—Smooth with large, horizontal lenticels.
- *Bark color.*—Plate 46, A 1 (Cement National Grey) as the predominant color with some slight reddish-brown tones.
- *Lenticels.*—Length: 2 to 5 cm. Width: 2 to 4 mm. Color: Plate 15, C 4 (Pelt and Pampas). Density: High.

Branches:
- *Diameter.*—Variable; from 1 to 2.5 cm. in the same growing season.
- *Surface texture.*—Smooth in the current season with scarfskin as maturity advances.
- *Color.*—Plate 6, A 9 (Manon).
- *Form.*—Circular in diameter.
- *Average angle.*—Acute.
- *Bud arrangement.*—Helicoidal throughout the branch.
- *Lenticels.*—Length: 0.5 to 0.8 mm. in the first year of growth; 1 to 2 mm. after the second year of growth. Width: 0.2 to 0.5 mm. Shape: Elongated horizontally. Density: Low. Color: Plate 5, A 7.

Leaves:
- *Length.*—10 to 14 cm.
- *Width.*—3 to 4.5 cm.
- *Form.*—Lanceolate.
- *Texture.*—Smooth.
- *Thickness.*—Thin to medium.
- *Base.*—Acute.
- *Apex.*—Acute.
- *Margin.*—Crenate.
- *Pubescence.*—Upper surface: Absent. Lower surface: Absent.
- *Color.*—Young leaves: Upper surface: Plate 22, L 7 (Art Green). Lower surface: Plate 22, H 7 (Garland Green). Mature leaves: Upper surface: Plate 23, J 7. Lower surface: Plate 22, L 7.
- *Petiole.*—Shape: Straight with a central groove along the upper side with 1 or 2 very small sized nectaries near the base of the leaf; sometimes the nectaries are absent. Length: 10 to 15 mm. Diameter: 1 to 2 mm. Color: Plate 20, K 6 (Piquant Green).
- *Veins.*—Venation type: Tree type disposition. Color: Upper surface: Plate 20, K 5 (Absinthe Green). Lower surface: Plate 20, H 5.

Flower buds:
- *Pedicel.*—Length: 0.5 to 0.8 mm. Diameter: 0.6 to 0.8 mm. Color: Plate 7, J 8 (Domingo).
- *Bud.*—Length: 3 to 4 mm. Width: 2 to 3 mm. Shape: Ovoid to round. Color: Plate 7, L 8 (Mascara).

Flowers:
- *Bloom timing.*—February 18th in Barcelona, Spain.
- *Blooming period.*—10 to 15 days.
- *Pollination requirements.*—None.
- *Number of flowers per raceme.*—Normally individual, occasionally 2 present.
- *Fragrance.*—Rose-like.
- *Petals.*—Number: 5. Length: 8 to 11 mm. Width: 5 to 8 mm. Shape: Rounded. Aspect: Cupped upwards and inwards without overlapping. Margin: Even. Texture and appearance: Smooth.
- *Color.*—When opening: Upper surface: Plate 1, A 1. Lower surface: Plate 1, A 1. Fully opened: Upper surface: Plate 1, A 1. Lower surface: Plate 1, A 1.
- *Sepals.*—Shape: Elliptic. Margin: Smooth. Texture: Pubescent at the edges. Length: 3 to 5 mm. Width: 2 to 4 mm. Color: Upper surface: Plate 4, L 9. Lower surface: Plate 4, L 8.
- *Stamens.*—Number (per flower): 18 to 20. Filament length: 8 to 11 mm.
- *Anthers.*—Shape: Kidney-shaped. Length: 1 to 1.5 mm. Color: Plate 12, J 5 (Light Stone).
- *Pollen.*—Color: Plate 12, H 6 (Roe). Amount: Abundant.
- *Pistils.*—Length: 8 to 9 mm.
- *Style.*—Length: 6 to 7 mm. Color: Plate 1, D 1.
- *Stigma.*—Shape: Rounded to ovoid. Color: Plate 12, L 3 (Pyrite Yellow).

Fruit: None present.

Stem:
- *Length.*—Variable, but can be long (20 cm. to 1.5 meters).
- *Width.*—4 to 8 mm.
- *Color.*—Plate 6, J 11 (Copper Leaf).

Use: As a rootstock for peach, nectarine, and almond varieties.
Winter hardiness: Hardy (under the conditions in Spain).
Bud winter hardiness: Medium.
Drought tolerance: Moderately tolerant.

I claim:

1. A new and distinct variety of hybrid peach-almond plant, as illustrated and described herein.

* * * * *